(12) United States Patent
Saito et al.

(10) Patent No.: US 8,187,579 B2
(45) Date of Patent: May 29, 2012

(54) THICKENING AGENT

(75) Inventors: Keitaro Saito, Kawasaki (JP); Tatsuya Hattori, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 421 days.

(21) Appl. No.: 12/045,260

(22) Filed: Mar. 10, 2008

(65) Prior Publication Data

US 2009/0030092 A1 Jan. 29, 2009

(30) Foreign Application Priority Data

Mar. 9, 2007 (JP) ................................. 2007-059558

(51) Int. Cl.
*A61Q 5/00* (2006.01)
(52) U.S. Cl. ....................................... 424/70.1; 514/538
(58) Field of Classification Search ........................ None
See application file for complete search history.

(56) References Cited

U.S. PATENT DOCUMENTS

| | | | | |
|---|---|---|---|---|
| 3,969,087 A * | 7/1976 | Saito et al. | ....................... | 44/270 |
| 5,403,517 A * | 4/1995 | Horinishi et al. | .......... | 424/70.21 |
| 2004/0096412 A1 | 5/2004 | Uehara et al. | | |
| 2005/0232893 A1 * | 10/2005 | Kaharu et al. | ............. | 424/70.27 |
| 2007/0265347 A1 | 11/2007 | Ueyama et al. | | |

FOREIGN PATENT DOCUMENTS

| | | |
|---|---|---|
| EP | 1 586 298 | 10/2005 |
| EP | 1 746 141 | 1/2007 |
| JP | 2003-082387 | 3/2003 |

OTHER PUBLICATIONS

U.S. Appl. No. 12/167,556, filed Jul. 3, 2008, Saito, et al.
Office Action issued Aug. 30, 2011, in Japanese Patent Application No. 2007-059558.

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

Thickening agents which containing a specific N-acylamino acid (component A) and a specific amideamine (component B) are capable of generating, when used in combination with a wide variety of oily bases including a hydrocarbon oil and silicone, a creamy thickening composition having a practical dissolution temperature and a smooth feeling in use when applied to the skin.

18 Claims, No Drawings

THICKENING AGENT

CROSS REFERENCES TO RELATED APPLICATIONS

This application claims priority to Japanese Patent Application No. 059558/2007, filed on Mar. 9, 2007, which is incorporated herein by reference in its entirety.

BACKGROUND OF THE INVENTION

1. Field of the Invention

This invention relates to thickening agents useful for thickening a composition containing an oily base. The present invention also relates to compositions which contain such a thickening agent and an oily base.

2. Discussion of the Background

As a thickening agent or a solidifying agent for an oily base that is not soluble in water, a polyamide resin, 12-hydroxystearic acid, fatty acid dextrin, fatty acid inulin, fatty acid glycerin, dibenzylidene-D-sorbitol, acylamino acid, an acylamino acid amine salt, and the like have heretofore been known in general. However, although these thickening agents or solidifying agents are capable of thickening or solidifying specific oily agents, they are not capable of thickening or solidifying a wide variety of oily agents.

In the case of using an acylamino acid as a solidifying agent (see, JP-A-51-91884), the obtained gel composition is not smooth when applied to the skin and does not provide a good feeling in use.

Also, in the case of using acylalanine among acylamino acids as a thickening agent (see, JP-A-2004-100826), although acylalanine thickens silicone, acylalanine is not always satisfactory since it requires strong stirring during cooling in preparation of a gel oil.

The use of an acylamino acid amine salt as a gelatinizing agent has been known (see, JP-A-51-19139). Although an alkylamine salt is used as the amine salt of acylamino acid, the amine salt is considerably limited in the types of oily agents it can gelatinize, and the capability of the amine salt as a thickening agent is not always satisfactory since it is necessary to reinforce its gelatinizing capability by using waxes such as vaseline, lanoline, beeswax in combination in an amount of several times that of the amine salt in the case of using the amine salt for cosmetics such as a hair-styling agent and a cleansing gel.

Cosmetics containing N-acyl-L-glutamic acid dibutylamide have been reported as a gelatinizing agent (see, JP-A-2002-31697). N-acyl-L-glutamic acid dibutylamide is known to gelatinize various oily agents such as a hydrocarbon oil, an ester oil, and a silicone oil. However, the cosmetics have problems of: a low solubility to ordinary oily agents; a high temperature of about 150° C. is required for dissolving the gelatinizing agents; and they are not smooth when applied to the skin due to a hard and crumbly form of the obtained thickening composition.

Thus, there has been a strong demand for a thickening agent capable of thickening a wide variety of oily bases including a hydrocarbon oil and silicone as well as of generating a thickening composition having a practical dissolution temperature and excellent comfortableness in use.

SUMMARY OF THE INVENTION

Accordingly, it is one object of the present invention to provide novel to provide thickening agents.

It is another object of the present invention to provide novel thickening agents capable of thickening a wide variety of oily bases including a hydrocarbon oil and silicone as well as of generating a creamy thickening composition having a practical dissolution temperature and providing a good feeling in use as being smoothly applied to the skin.

It is another object of the present invention to provide novel thickening compositions which contain such a thickening agent and an oily base.

These and other objects, which will become apparent during the following detailed description, have been achieved by the inventors' discovery that it is possible to attain the object by using a thickening agent which contains at least one specific N-acylamino acid (component A) and at least one specific amideamine (component B).

Thus, the present invention provides the following aspects.

(1) A thickening agent, comprising:
(A) at least one N-acylamino acid; and
(B) at least one amideamine, represented by formula (I):

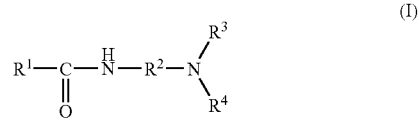

wherein $R^1$ represents a straight chain or branched chain hydrocarbon group having 11 to 25 carbon atoms; $R^2$ represents an alkylene group having 1 to 3 carbon atoms; and each of $R^3$ and $R^4$ independently represents an alkyl group having 1 to 3 carbon atoms.

(2) The thickening agent according to (1), further comprising at least one fatty acid.

(3) The thickening agent according to (1) or (2), wherein said at least one N-acylamino acid is one or more members selected from the group consisting of acylglycine, acylalanine, acylvaline, acylleucine, acylisoleucine, acylphenylalanine, and a mixture thereof.

(4) The thickening agent according to any one of (1) to (3), wherein $R^1$ has 17 to 21 carbon atoms.

(5) A thickening composition, comprising a thickening agent defined in any one of (1) to (4) and an oily base.

By using the thickening agent containing the specific acylamino acid (component A) and amideamine (component B), it is possible to provide a thickening agent capable of thickening a wide variety of oily bases including a liquid paraffin, an ester oil, and silicone as well as of generating a creamy thickening composition having a practical dissolution temperature and providing a good feeling in use as being smoothly applied to the skin. Thus, it is possible to provide a thickening composition having excellent feeling in use and transparency.

DETAILED DESCRIPTION OF THE PREFERRED EMBODIMENTS

Thus, in a first embodiment, the present invention provides novel thickening agents which contain at least one acylamino acid (component A) and at least one amideamine (component B).

The amino acid to be used for acylamino acid (component A) of this invention is not particularly limited insofar as the amino acid is capable of thickening, and specific examples thereof include neutral amino acids such as glycine, alanine, valine, leucine, isoleucine, and phenylalanine; acidic amino acids such as asparaginic acid and glutamic acid; and the like. From the viewpoint of obtaining a thickening composition providing a smooth feeling in use when applied to the skin, the neutral amino acids and the acidic amino acids are preferred, among which glycine, alanine, valine, leucine, isoleucine, phenylalanine, asparaginic acid, and glutamic acid are preferred, and glycine, alanine, valine, leucine, isoleucine, and phenylalanine are particularly preferred.

The acyl group to be used for the acylamino acid (component A) may be of a straight chain or branched chain. The acyl group derived from a saturated or unsaturated fatty acid having 8 to 18 carbon atoms may be used, and examples thereof include an octanoyl group, a 2-ethylhexanoyl group, a nonanoyl group, a decanoyl group, a lauroyl group, a myristoyl group, a palmitoyl group, a stearoyl group, an oleoyl group, and the like. An acyl group derived from fatty acid of a single component, and acyl groups derived from mixed fatty acids obtainable from natural fatty acids such as coconut oil fatty acid, caster oil fatty acid, olive oil fatty acid, and palm oil fatty acid or from synthetic fatty acids (including branched chain fatty acid) may be used. From the viewpoints of obtaining a smooth thickening composition providing a good feeling in use and having excellent transparency, lauroyl, 2-ethylhexyl, and coconut oil fatty acid are most preferable.

It is possible to prepare the acylamino acid (component A) of this invention by a combination of known technologies. For example, it is possible to obtain the N-acylamino acid by the Schotten-Bauman reaction for reacting a long chain fatty acid chloride with an amino acid under a basic atmosphere.

The amideamine (component B) used in this invention is a compound represented by the general formula (I):

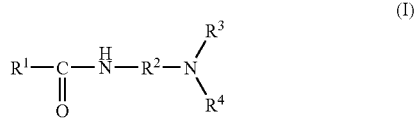

(I)

wherein $R^1$ represents a straight chain or branched chain hydrocarbon group having 11 to 25 carbon atoms; $R^2$ represents an alkylene group having 1 to 3 carbon atoms; and each of $R^3$ and $R^4$ independently represents an alkyl group having 1 to 3 carbon atoms.

The hydrocarbon group represented by $R^1$ may be of a straight chain or a branched chain. For example, the hydrocarbon group is a lauroyl group, a myristoyl group, a palmitoyl group, a stearoyl group, an oleoyl group, a behenyl group, or the like.

Specific examples of the amideamine compound represented by the general formula (I) include dimethylaminopropylamide laurate, dimethylaminopropylamide myristate, dimethylaminopropylamide stearate, dimethylaminopropylamide behenate, and the like.

It is possible to prepare the amideamine (component B) of the present invention by a combination of known technologies. For example, it is possible to produce the amideamine by an aminolysis reaction for reacting fatty acid alkylester with diamine. Also, commercially available products such as Katinal manufactured by Toho Chemical Industries, Co., Ltd. and NIKKOL amideamine manufactured by Nikko Chemicals Co., Ltd. may be used.

From the viewpoint of achieving a creamy and smooth feeling in use, the mixing ratio (molar ratio) between the acylamino acid (component A) and the amideamine (component B), the (component A)/(component B) ratio, may preferably be 90/10 to 20/80, particularly preferably 80/20 to 60/40.

A total content (wt %) of the acylamino acid (component A) and the amideamine (component B) in the thickening agent of this invention as a whole is not particularly limited insofar as the thickening agent is capable of thickening, and a lowest content may preferably be 10%, more preferably 50%, particularly preferably 80% from the viewpoint of obtaining a uniform and smooth thickening composition. From the viewpoint of a spreading property in application and considering capability of thickening a wide variety of oily bases, a highest content may preferably be 100%, particularly preferably 98%.

By adding a specific higher fatty acid (component C) to the thickening agent of the present invention, it is possible to impart to a thickened matter smoothness in application as a feeling in use. As the higher fatty acid, those having 8 to 22 carbon atoms may be used. Specific examples thereof include octanoic acid, lauric acid, myristic acid, palmitic acid, stearic acid, isostearic acid, oleic acid, behenic acid, and the like. In addition to fatty acid of a single component, mixed fatty acids obtainable from natural fatty acids such as coconut oil fatty acid, caster oil fatty acid, olive oil fatty acid, and palm oil fatty acid, synthetic fatty acids (including branched chain fatty acid), and the like may also be used. From the viewpoint of not loosing the creamy appearance, octanoic acid, lauric acid, stearic acid, isostearic acid, behenic acid, and coconut oil fatty acid are preferred. From the viewpoint of obtaining a smooth feeling in application, lauric acid, stearic acid, isostearic acid, and behenic acid are particularly preferred.

The content (wt %) of the component C with respect to the total weight of the component A and the component B in this invention is not particularly limited insofar as thickening is achieved. From the viewpoint of obtaining smooth feeling in application, a lowest content may preferably be 0.1%, more preferably 1%, particularly preferably 5%. From the viewpoint of penetration to the skin, a highest content may preferably be 1,000%, more preferably 100%, particularly preferably 50%.

The thickening agent of this invention may be used as a thickening composition when used for an oily base.

Specific examples of the oily base to be used for the thickening composition of this invention include, though not particularly limited to insofar as the thickening agent is satisfactorily dissolved by heating and forms a thickened matter when cooled to a room temperature, silicones such as dimethylpolysiloxane, methylphenylpolysiloxane, octamethylcyclotetrasiloxane, decamethylcyclopentasiloxane, and dodecamethylcyclohexasiloxane; higher alcohols such as cetyl alcohol, isostearyl alcohol, lauryl alcohol, hexadecyl alcohol, octyldodecanol; polyvalent alcohols such as glycerin, sorbitol, ethyleneglycol, propyleneglycol, polyethyleneglycol, and panthenol; esters such as myristyl myristate, hexyl laurate, decyl oleate, isopropyl myristate, hexyldecyl dimethyloctanate, glycerin monostearate, diethyl phthalate, ethyleneglycol monostearate, octyl oxystearate, and alkylester benzoate; hydrocarbons such as liquid paraffin, polyisobutene, squalane; oils such as a mink oil, a cacao oil, a coconut oil, a palm kernel oil, a camellia oil, a sesame oil, a caster oil, and an olive oil; ethylene.α-olefin cooligomer; and the like. From the viewpoint of obtaining a creamy composition, silicones, hydrocarbons, esters, and oils are preferred.

From the viewpoint of achieving smoothness in application as a feeling in use, silicones, hydrocarbons, and oils are particularly preferred.

The content (wt %) of the thickening agent with respect to the thickening composition as a whole is not particularly limited insofar as thickening is achieved. From the viewpoint of solubility of the thickening agent and good appearance, the content may preferably be 0.1% to 20%. From the viewpoint of enhancing freedom degree in formulation, the content may more preferably be 0.3% to 10%. From the viewpoint of obtaining a uniform and smooth thickening composition, the content may particularly preferably be 0.5% to 5%.

The content of the oily base with respect to the whole thickening composition of this invention may preferably be 10% to 99.9% though not particularly limited insofar as thickening is achieved. In the case where the content is less than 10%, the feeling in use tends to be deteriorated. In the case where the content exceeds 99.9%, there is a tendency of failing to achieve satisfactory viscosity.

It is possible to enhance stability to heat and temperature of the thickening composition by using another gelatinizing agent in combination with the thickening composition of this invention. Examples of such gelatinizing agent include, though not particularly limited to, acylglutamic acid diamides such as a polyamide resin, 12-hydroxystearic acid, sodium stearate, dibenzylidene-D-sorbitol, fatty acid dextrin, fatty acid glycerin, N-2-ethylhexyl-L-glutamate dibutylamide, and N-lauroyl-L-glutamate dibutylamide; acylglutamine esters such as N-lauroyl-L-glutamine isopropylester; and the like.

As a production method for the thickening composition of this invention, the thickening agent and the oily base are heated to 60° C. to 100° C. with stirring until the mixture forms a uniform solution, followed by cooling to obtain a desired thickening composition. In the case where the mixture is dissolved at a low temperature lower than 60° C., the thickening composition can be problematic from the viewpoint of storage stability. In the case where the mixture is dissolved at a temperature higher than 100° C., it can be unfavorable to produce the thickening composition comprising substances having poor heat stability and volatile components.

The thickening composition of this invention may be used as a cosmetics as being mixed with various components usable for cosmetics in a range that does not inhibit the effect of this invention. Examples of the cosmetics include various chelating agents, surfactants, various additives, various powders, antiperspirant components, and the like. The thickening composition to be used in this invention means those comprising a thickening agent and an oily base in a narrow sense and means cosmetics containing a thickening agent, an oily base, and other components in broad sense.

The cosmetics of this invention may be used as cosmetics such as a hair gel, a skin cream, and a makeup without particular limitation.

Other features of the invention will become apparent in the course of the following descriptions of exemplary embodiments which are given for illustration of the invention and are not intended to be limiting thereof.

EXAMPLES

Production Example 1

Production of Thickening Agent Containing N-Lauroylglycine (Component A)/Dimethylaminopropylamide Stearate (Component B)

After dissolving 5.1 g of lauroylglycine and 7.3 g amideamine into 50 g of methanol, hot filtration was performed, followed by elimination of the solvent. The thus-obtained white solid matter was recrystallized from methanol/diethylether to obtain a target matter.

Production Example 2

Production of Thickening Composition

A thickening agent was prepared by mixing acylamino acid (component A) and amideamine (component B) in the same manner as in Production Example 1 at a target ratio. The prepared thickening agent was added to a solvent to be dissolved into the solvent by heating with stirring, and the mixture was left to cool to 25° C. without stirring, thereby obtaining a thickening composition.

Examples 1 to 7 and Comparative Examples 1 and 2

Investigation on Ratios between Acylamino Acid (Component A) and Amideamine (Component B)

Thickening agents were prepared by changing the N-lauroylglycine (component A)/dimethylaminopropylamide stearate (component B) ratio, and 2 wt % of each of the thus-obtained thickening agents was added to a solvent to be dissolved into the solvent by heating, followed by cooling to 25° C. without stirring. The form of the thus-obtained thickening compositions were evaluated. The form evaluation was indicated as follows. Creamy: •; thickened to a liquid form or solidified to a solid form: ○; and precipitated and dissolved without being thickened nor solidified: x. The dissolution temperature was evaluated as follows. Dissolved at 90° C.: •; dissolved at 100° C.: ○; and dissolved at a temperature of 110° C. or more: x.

The evaluation results of the forms of the thickening compositions and the dissolution temperatures of the thickening agents in the case of using an oily agent and liquid paraffin are shown below in Table 1.

TABLE 1

|  | Comp. Ex. 1 | Ex. 1 | Ex. 2 | Ex. 3 | Ex. 4 | Ex. 5 | Ex. 6 | Ex. 7 | Comp. Ex. 2 |
|---|---|---|---|---|---|---|---|---|---|
| Component A/Component B Ratio (Molar Ratio) | 100/0 | 90/10 | 80/20 | 70/30 | 60/40 | 50/50 | 40/60 | 20/80 | 0/100 |
| Form | x | • | • | • | • | ○ | ○ | ○ | x |
| Dissolution temperature | x | ○ | • | • | • | • | • | • | • |

From the results shown in Table 1, it is understood that a preferable N-lauroylglycine (component A)/dimethylaminopropylamide stearate (component B) mixing ratio is 90/10 to 20/80, and that the form of the thickening composition and the dissolution of the thickening agent are excellent when the (component A)/(component B) ratio is 80/20 to 60/40. Also, the thickening composition production method has the advantage of not requiring stirring during cooling.

Examples 8 to 10 and Comparative Examples 3 to 8

Thickening Experiment

Evaluation of forms and transparencies of thickened matters were conducted by using thickening compositions each prepared by using 2 wt % of a thickening agent containing the component A and the component B in the component A/component B ratio of 70/30 by mol. The evaluation of forms was as follows. Thickened to be creamy: ○; solidified to a solid form: Δ; and precipitated and dissolved without being thickened nor solidified: x. As used herein, creamy means smooth and having fluidity, and solid form means not having fluidity and crumbled when stress is applied.

The results of thickening experiment using various oily agents are shown in Table 2.

TABLE 2

|  | Ex. 8 Thickening agent 1 | Ex. 9 Thickening agent 2 | Ex. 10 Thickening agent 3 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|---|
| Silicone | ○ | ○ | ○ | x | x | x | x | x | x |
| Isopropyl Myristate | ○ | ○ | ○ | x | x | x | x | x | x |
| Liquid paraffin | ○ | ○ | ○ | x | Δ | x | Δ | Δ | x |

The thickening agents and compounds evaluated herein are as follows.

Thickening agent 1: thickening agent comprising N-lauroylglycine (component A)/dimethylaminopropylamide stearate (component B)

Thickening agent 2: thickening agent comprising N-lauroyl-L-phenylalanine (component A)/dimethylaminopropylamide behenate (component B)

Thickening agent 3: thickening agent comprising N-2-ethylhexanoyl-L-phenylalanine (component A)/dimethylaminopropylamide behenate (component B)

Comparative Example 3: N-lauroylglycine (component A)

Comparative Example 4: Dimethylaminopropylamide stearate (component B)

Comparative Example 5: $N^\alpha,N^\epsilon$-dilauroyl-L-lysine

Comparative Example 6: $N^\alpha,N^\epsilon$-dilauroyl-L-lysine stearylamine salt Comparative Example 7: $N^\alpha,N^\epsilon$-dilauroyl-L-lysine octylamine salt Comparative Example 8: N-lauroylglycine dibutylamine salt From Table 2, it is understood that it is possible to obtain smooth and creamy thickening compositions by adding the thickening agents of Examples. In contrast, the comparative compounds are undesirable since they are dissolved or precipitated into the oily agent or have fragile forms.

Examples 11 and 12

Evaluation of Fatty Acid-Added Thickening Compositions

The feelings of a thickening composition when applied to the skin was evaluated based on the following evaluation standard and by five specialized panelists, the thickening composition being prepared by adding a fatty acid (component C) to a thickening agent comprising N-2-ethylhexanoyl-L-phenylalanine (component A)/dimethylaminopropylamide behenate (component B) and having a (component A)/(component B) ratio of 70/30 (molar ratio).

Penetration to the Skin in Application (Scale of 1 to 3)

Standard 3: remarkably good penetration

2: good penetration

1: poor penetration

As the evaluation results, the one having an average point of 2.6 or more is indicated by •; the one having an average point of 2.1 to 2.5 is indicated by ○; and the one having an average point of 2.0 or less is indicated by x. The results are shown below in Table 3.

TABLE 3

|  | Ex. 11 | Ex. 12 |
|---|---|---|
|  | Thickening Agent 3 | |
| N-2-ethylhexanoyl-L-phenylalanine (Component A)/ dimethylaminopropylamide behenate (Component B) | 2 | 1.8 |
| Stearic Acid (Component C) | 0 | 0.2 |
| Liquid paraffin | 98 | 98 |
| Penetration to Skin | ○ | • |

As is apparent from Table 3, it is possible to obtain a thickening composition having increased penetration by adding the small amount of fatty acid (component C) to the thickening agent comprising acylamino acid (component A) and amideamine (component B).

Formulation Example 1

Hair Gel

TABLE 4

| Thickening Agent 2 | 2.0 |
|---|---|
| Liquid paraffin | 40.0 |
| Cyclomethicone | 20.0 |
| Dimethicone | 20.0 |
| Isononyl Isononanate | 17.7 |
| Stearic Acid | 0.2 |
| Tocopherol | 0.1 |
|  | 100.0 |

INDUSTRIAL APPLICABILITY

The thickening agent of the present invention is capable of thickening a wide variety of oily bases including a hydrocarbon oil and silicone, and it is considerably significant that the thickening agent enables the provision of creamy cosmetics having a practical dissolution temperature and smoothness when applied to the skin as a feeling in use, such as a hair gel, a skin cream, and a makeup.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A thickening composition, comprising:
   (1) a thickening agent, comprising:
   (A) N-acylaminoacid, wherein the N-acylaminoacid is selected from the group consisting of N-lauroylglycine, N-lauroyl-L-phenylalanine and/or N-2-ethylhexanoyl-L-phenylalanine, and
   (B) amideamine, wherein the amideamine is selected from the group consisting of dimethylaminopropylamide stearate and/or dimethylaminopropylamide behenate,
   wherein (A) and (B) are present in a molar ratio of (A)/(B) 80/20 to 60/40; and
   (2) at least one oily base comprising at least one member selected from the group consisting of dimethylpolysiloxane, methylphenylpolysiloxane, octamethylcyclotetrasiloxane, decamethylcyclopentasiloxane, dodecamethylcyclohexasiloxane, cetyl alcohol, isostearyl alcohol, lauryl alcohol, hexadecyl alcohol, octyldodecanol, glycerin, sorbitol, ethyleneglycol, propyleneglycol, polyethyleneglycol, panthenol, myristyl myristate, hexyl laurate, decyl oleate, isopropyl myristate, hexyldecyl dimethyloctanate, glycerin monostearate, diethyl phthalate, ethyleneglycol monostearate, octyl oxystearate, alkylester benzoate, liquid paraffin, polyisobutene, squalane, mink oil, cacao oil, coconut oil, palm kernel oil, camellia oil, sesame oil, a caster oil, olive oil, and a mixture thereof.

2. The thickening composition according to claim 1, wherein the thickening agent further comprising at least one fatty acid.

3. The thickening agent according to claim 2, wherein said at least one fatty acid is one or more members selected from the group consisting of octanoic acid, lauric acid, stearic acid, isostearic acid, behenic acid, coconut oil fatty acid, and a mixture thereof.

4. The thickening agent according to claim 2, which comprises said at least one fatty acid in an amount of 0.1 wt % to 1,000 wt %, based on the total weight of (A) and (B).

5. The thickening composition according to claim 2, which comprises said at least one fatty acid in an amount of 1 wt % to 100 wt %, based on the total weight of (A) and (B).

6. The thickening composition according to claim 2, which comprises said at least one fatty acid in an amount of 5 wt % to 50 wt %, based on the total weight of (A) and (B).

7. The thickening composition according to claim 1, which comprises said thickening agent in an amount of 0.1 to 20 wt %, based on the total weight of said thickening composition.

8. The thickening composition according to claim 1, which comprises said thickening agent in an amount of 0.3 to 10 wt %, based on the total weight of said thickening composition.

9. The thickening composition according to claim 1, which comprises said thickening agent in an amount of 0.5 to 5 wt %, based on the total weight of said thickening composition.

10. The thickening composition according to claim 1, wherein (A) is N-lauroylglycine.

11. The thickening composition according to claim 1, wherein (A) is N-lauroyl-L-phenylalanine.

12. The thickening composition according to claim 1, wherein (A) is N-2-ethylhexanoyl-L-phenylalanine.

13. The thickening composition according to claim 1, wherein (B) is dimethylaminopropylamide stearate.

14. The thickening composition according to claim 1, wherein (B) is dimethylaminopropylamide behenate.

15. The thickening composition according to claim 1, wherein (A) is N-lauroylglycine and (B) is dimethylaminopropylamide stearate.

16. The thickening composition according to claim 1, wherein (A) is N-lauroyl-L-phenylalanine and (B) is dimethylaminopropylamide behenate.

17. The thickening composition according to claim 1, wherein (A) is N-2-ethylhexanoyl-L-phenylalanine and (B) is dimethylaminopropylamide behenate.

18. The thickening composition according to claim 1, wherein said oily base comprises isopropyl myristate and/or liquid paraffin.

* * * * *